United States Patent [19]

Cain et al.

[11] Patent Number: 6,166,211

[45] Date of Patent: Dec. 26, 2000

[54] SEQUENTIAL BENZYLIC OXIDATIONS OF THE NALOXONE RING SYSTEM

[75] Inventors: Gary A. Cain; Spencer Drummond, Jr., both of Wilmington, Del.

[73] Assignee: Endo Pharmaceuticals, Inc., Chadds Ford, Pa.

[21] Appl. No.: 09/520,099

[22] Filed: Mar. 7, 2000

Related U.S. Application Data

[60] Provisional application No. 60/125,121, Mar. 19, 1999.

[51] Int. Cl.$^7$ .................................................. C07D 489/02
[52] U.S. Cl. .................................. 546/44; 546/45; 546/46
[58] Field of Search ................................ 546/45, 44, 46

[56] References Cited

PUBLICATIONS

Archer, S. et al. : 10–Ketonaltrexone and 10–Ketooxymorphone. J. Med. Chem. vol. 28, pp. 974–976, 1985.

Sagara, T. et al. : Design and synthesis of 10–oxo derivative of N–cyclopropylmethyl (–)–6–beta–acetylthiodihydronormorphine. Bioorganic & Medicinal Chem. Lett. vol. 5, pp. 1505–1508, 1995.

*Primary Examiner*—Alan L. Rotman
*Assistant Examiner*—Charanjit S. Aulakh
*Attorney, Agent, or Firm*—Schnader Harrison Segal & Lewis LLP

[57] ABSTRACT

The present invention pertains to a process for the preparation of the 10-keto analogs of morphinan compounds. In the case of compounds having a 3-hydroxyl group, the 3-methyl ether protected analog is synthesized by selective phenolic methylation in the presence of the basic amino group. When nalbuphine, morphine, or codeine is used as the starting material, the additional 6-hydroxyl group is protected using acetylation. The protected analog is selectively oxidized by treatment with cerium ammonium nitrate to provide the 10-(S)-hydroxy adduct. The 10-(S)-hydroxy adduct is further oxidized to the 10-keto analog. Any protecting groups that were added prior to oxidation are cleaved subsequent to oxidation to form the desired 10-ketomorphinan.

12 Claims, No Drawings

SEQUENTIAL BENZYLIC OXIDATIONS OF THE NALOXONE RING SYSTEM

CROSS-REFERENCE TO RELATED APPLICATIONS

This application is based on U.S. Provisional Application Ser. No. 60/125,121 filed Mar. 19, 1999.

BACKGROUND OF THE INVENTION

1. Field of the Invention

This invention relates to a process for forming 10-keto derivatives of morphinan compounds.

2. Description of the Related Art

Methods have been reported in the literature for the synthesis of a small number of structurally related 10-ketomorphinans. Methods using $CrO_3$ as an oxidant (S. Archer et al., J. Med. Chem. 28: 974–976, 1985, and H. Rapoport et al., J. Am. Chem., 77:4330–4335, 1955) suffer from extremely low yields. Methods which use $SeO_2$ as oxidant (R. T. Uyeda et al., Tetrahedron Lett., 30:5725–5728, 1989) necessitate rendering the ring nitrogen into a non-basic amide form, thereby adding extra synthetic steps. Commonly used methods for effecting 10-oxidations use a phenolic 3-methyl ether protected analog. The classical conditions for morphinan 3-methyl ether synthesis require the highly toxic, rather volatile dimethyl sulfate in aqueous NaOH (S. Archer et al., J. Med. Chem. 28: 974–976, 1985, and H. Rapoport et al., J. Am. Chem., 77:4330–4335, 1955).

Cerium ammonium nitrate (CAN) has been reported to effect benzylic oxidations on electron rich aromatic compounds in alcoholic (or HOAc) solutions to provide benzyl ether (or acetate) mono adducts (K. Isobe et al., Chem. Pharm. Bull 42: 197–1994). It is therefore an object of the present invention to apply these principals to find a useful oxidation scheme to provide the benzylic 10-hydroxyl adduct. Although CAN has been reported under certain conditions to oxidize simple toluenes to aldehydes and ketones (S. B. Lang et al., J. Chem. Soc. (C)2915, 1968 and references therein), no 10-keto adduct was observed by $^1H$ NMR in the crude oxidation product. The 10-(S)-alcohol was readily oxidized into the 10-ketone analog with the Dess-Martin periodinane (Dess, D. B. and Martin, J. C., J. Org. Chem. 48, 4155–4158, 1983; Dess, D. B. and Martin, J. C., J. Am. Chem Soc. 113, 7277–7287, 1991; Ireland, R. E. and Liu, L., J. Org. Chem. 58, 2899, 1993; Schrieber, S. L. and Meyer, S. D., J. Org. Chem. 59, 7549–7552, 1994). These pharmaceutical compounds are related to morphinans which have effects such as analgesia, sedation, mood alteration. The 10-keto morphinan compounds are the degradation products of morphinans and may therefore be related to the age and condition of the original morphinan compounds.

It is therefore an object of the present invention to provide a new and rapid method for the conversion of morphinan compounds into their 10-keto analogs. A further object of the invention is to provide a process which provides relatively high yield of the desired compounds. Another object is to provide a method that is relatively safe and avoids the use of highly volatile and toxic reagents.

SUMMARY OF THE INVENTION

The present invention pertains to a process for the preparation of the 10-keto analogs of morphinan compounds. In the case of compounds having a 3-hydroxyl group, the 3-methyl ether protected analog is synthesized by selective phenolic methylation in the presence of the basic amino group. When nalbuphine, morphine, or codeine is used as the starting material, the additional 6-hydroxyl group is protected using acetylation. The protected analog is selectively oxidized by treatment with cerium ammonium nitrate to provide the 10-(S)-hydroxy adduct. The 10-(S)-hydroxy adduct is further oxidized to the 10-keto analog. Any protecting groups that were added prior to oxidation are cleaved subsequent to oxidation to form the desired 10-ketomorphinan.

DETAILED DESCRIPTION

The morphinan compounds useful in the method of the present invention have the general Formulas I and Ia.

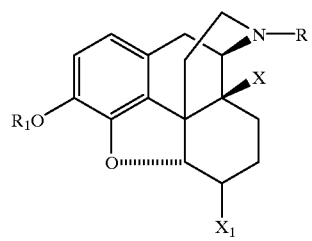

(I)

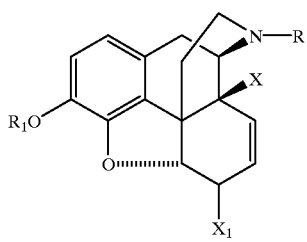

(Ia)

Where

R is $C_1$–$C_4$ alkyl or alkenyl, $C_3$–$C_4$ cycloalkyl, $C_3$–$C_4$ cycloalkyl alkyl, or $C_3$–$C_4$ cycloalkyl carbonyl $R_1$ is H or $C_1$–$C_4$ alkyl X is H or OH $X_1$ is OH or=O The formulas I and Ia differ only in a single or double bond between the numbers 7 and 8 carbons. Formula Ia represents morphine (where R is $CH_3$, X is H, $X_1$ is OH, and $R_1$ is H) and codeine, and Formula I represents oxymorphone, hydromorphone, nalbuphine, oxycodone, hydrocodone, naltrexone, and naloxone. The method is useful for other compounds f this family as well. The method of the present invention is effective for compounds of both formulas I and Ia. The method does not depend on which form the compound takes, whether Formula I or Ia, but rather the method is the same for compounds of either formula. Therefore, for simplicity, the method will be illustrated with respect only to compounds of the Formula I. It should be understood, however, that the method applies equally to compounds of Formula Ia.

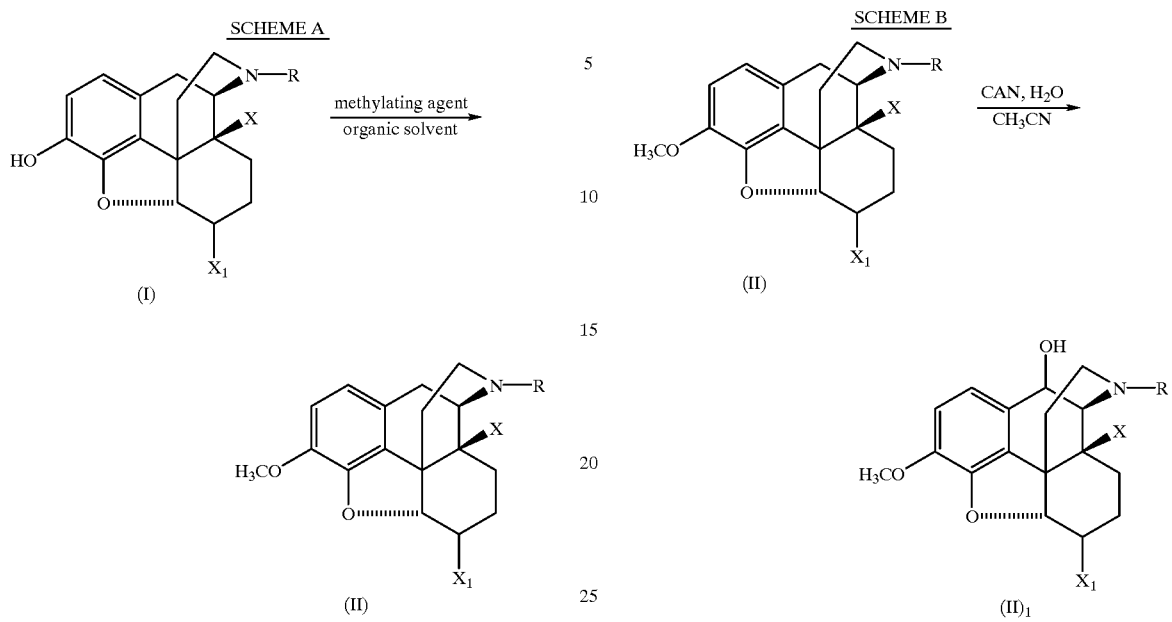

The first step of the process involves protection of the parent morphinan compound by synthesis of the phenolic 3-methyl ether analog, except in the case of oxycodone or codeine, which start with a methyl ether at the 3 position ($R_1$ is $CH_3$). Thus scheme A shows the starting material where $R_1$ of Formula I is H. This is accomplished by reacting the free base of the parent compound with a methylating agent in the presence of a base in a suitable organic solvent as shown in Scheme A. The methylating agent may be a typical methylating agent, such as dimethyl sulfate, methyl iodide, methyl trifluoromethane sulfonate, methyl para-toluene sulfonate or methyl bromide. The base may be an amine, a trialkylamine, sodium hydride, lithium diisopropyl amide (LDA), a strong inorganic base such as NaOH, or a weaker base such as a carbonate (Na, Li, Cs, K, Ca, Mg, Ba). The solvent may be any suitable non-reactive, preferably polar, organic solvent. DMF is a preferred organic solvent.

When nalbuphine, codeine, or morphine is used as the parent compound, an acetylation step is performed subsequent to the methylation (if required) to protect the additional hydroxyl group at the 6 position. This acetylation is performed upon the 3-methyl ether using an acetylating agent in the presence of a base and a catalyst in an organic solvent. For this reaction, acetic anhydride is a preferred acetylating agent although acetyl chloride or other acetylating agent would be acceptable. Triethylamine is a preferred base for the reaction, but inorganic bases such as the carbonates mentioned above would also be acceptable. The preferred solvent is a polar organic solvent, and chloroform is particularly preferred. 4-dimethyl amino pyridine (4-DMAP) is a preferred catalyst.

The protected compound (Formula II where $X_1$ is=O or acetyl) is reacted with Ceric ammonium nitrate (CAN) in the presence of water to produce the 10-alcohol intermediate, Formula III as shown in Scheme B. The ability of CAN to effect this benzylic oxidation in the presence of the generally oxidation prone olefin and trialkylamine groups is particularly noteworthy.

A polar organic solvent, such as acetonitrile, dichloromethane, and others may be used as a co-solvent. The isolated yield of the reaction tends to be low, due to the considerable difficulty in separating the organic product solution from the thick, gel-like cerium salt species. Optionally, an inert solid adsorbent such as Celite may be used to help isolate the desired product. The addition of our inorganic base will help increase the yield by driving the reaction due to the increase in free hydroxyl ions.

A second oxidation step is performed to oxidize the 10-alcohol to the 10-ketone analog. This reaction may be performed using alternate oxidizing conditions such as a Swern oxidation. Preferably, the oxidizing agent is small because steric considerations will limit the ability of the oxidizing agent to reach the hydroxyl group. Dess-Martin periodinane is the preferred oxidizing agent at this step.

After purification of the 10-keto product, any methyl and/or acetyl groups that have been added to protect the hydroxyl groups at the 3 and/or 6 positions are removed to produce the desired 10-ketomorphinan final product. When the phenolic 3-methyl ether protected analog is used for the oxidations, standard demethylation conditions may be used for deprotection, such as reaction with a metal cyanide, metal halide, or mercaptide in an inert solvent at elevated temperatures (about 100–250° C.). Deprotection may also be accomplished by reacting the protected compound with HBr, HF, HCl, or HI in water or acetic acid. A preferred method of deprotection is the use of standard $BBr_3$ conditions. In this reaction, the protected compound is reacted with boron tribromide (preferred) or other boron trihalide in an inert solvent, such as dichloromethane or chloroform.

When the hydroxyl group at the 3 position is protected by a methylation step and the hydroxyl group at the 6 position is protected by acetylation, a single reaction in any of the standard deprotection conditions described above may be used to remove both the 3-methyl and 6-acetyl protecting groups to produce the desired final product. Alternatively, stepwise reactions may be performed in which the acetyl group is specifically cleaved in the first step, followed by a deprotection step that serves to remove the remaining 3-methyl protecting group. Specific removal of the 6-acetyl group may be accomplished by reaction with a metal hydroxide (such as NaOH) or metal carbonate (such as potassium carbonate) in a polar solvent, such as methanol. The 3-methyl group may be removed by any of the standard deprotection methods described above.

If, as in the case of codeine, the starting compound already possesses a methyl ether at the 3 position and contains a hydroxyl group at the 6 position, only the 6-hydroxyl group requires protection prior to oxidation. Protection of the 6-hydroxyl group is accomplished by acetylation. After the sequential oxidations are completed, the desired product is formed by specific de-acetylation using a metal hydroxide (such as NaOH) or metal carbonate (such as potassium carbonate) in a polar solvent (such as methanol), which removes the 6-acetyl protecting group, but does not cleave the 3-methyl ether. If the starting compound contains no hydroxyl at either the 3 or the 6 position, as in the case of oxycodone, no protections or deprotections are necessary; carrying out the sequential oxidations is sufficient to produce the desired 10-keto product.

EXAMPLE 1

Preparation of 10-ketonaloxone.

Naloxone free base (20 g, 61 mmol), powdered $K_2CO_3$ (8.5 g, 62 mmol), and methyl p-toluenesulfonate (11.4 g, 61 mmol) were stirred in DMF (60 mL) at 65° C. overnight. TLC analysis indicated incomplete reaction. Additional $K_2CO_3$ (4.0 g, 29 mmol), and methyl p-toluenesulfonate (5.2 g, 28 mmol) were then added in portions over the next 48 h until TLC indicated complete consumption of naloxone. The mixture was concentrated, then extracted several times with EtOAc and water. The combined organic extracts were shaken with brine, then dried ($Na_2SO_4$), filtered, concentrated, and dried to produce naloxone 3-methyl ether (20 g, 96% yield) as a tan solid, mp 115–117° C. $^1H$ NMR ($CDCl_3$) δ6.71 (d, 1H, J=8 Hz), 6.64 (d, 1H, J=8 Hz), 5.89–5.76 (m, 1H), 5.25–5.17 (m, 2H), 5.03 (br s, 1H), 4.67 (s, 1H), 3.90 (s, 3H), 3.17–2.97(m, 5H), 2.62–1.56 (m, 8H). $^{13}C$ NMR ($CDCl_3$) δ208.34, 145.01, 142.94, 135.13, 129.47, 124.88, 119.38, 118.04, 115.07, 90.32, 70.23, 62.28, 57.63, 56.87, 50.72, 43.30, 36.11, 31.41, 30.56, 22.70. IR υ3376, 1720 cm$^{31\ 1}$. UV (MeOH) 283 (1400), 230 (9100) nm. $[\alpha]^{25}_D$ –214° (c 0.274, MeOH). MS (CI, $NH_3$) m/z 342 (base, MH$^+$). HRMS (CI, $NH_3$) m/z (MH$^+$) calcd for $C_{20}H_{24}NO_4$ 342.1705, found 342.1688. Anal. Calcd. for $C_{20}H_{23}NO_4$: C, 70.36; H, 6.79; N, 4.10. Found: C, 70.40; H, 6.78; N, 4.10.

Naloxone 3-methyl ether (20 g, 59 mmol) and CAN (129 g, 240 mmol) were stirred overnight in a mixture of water (30 mL) and $CH_3CN$ (590 mL) at ambient temperature. Solid $Na_2CO_3$ (55 g, 500 mmol) and a large amount of Celite were slurried into the reaction mixture, which was then filtered through additional Celite and rinsed well with $CH_3CN$. After concentrating the filtrate, the residue was shaken with EtOAc and 1 M NaOH (500 mL), which formed a thick gel. Celite was added and the mixture shaken to homogenize. This slurry was filtered through more Celite and rinsed thoroughly with more EtOAc and water. The resulting solution was shaken in a separatory funnel, phases separated, and the aqueous phase extracted further with fresh EtOAc (2x). The combined organics were extracted with half-saturated brine, dried ($Na_2SO_4$), filtered, and concentrated. The crude product mixture was purified by careful flash chromatography on silica gel, eluting with a gradient of $CHCl_3$ to 1:1 EtOAc/$CHCl_3$. Concentration of the separated major component fractions yielded recovered naloxone 3-methyl ether (10%) and 10-(S)-hydroxynaloxone 3-methyl ether (4.9 g, 23%) as a pale yellow foamy solid. IR υ3480, 3366, 1720 cm$^{-1}$. Anal. Calcd. for $C_{20}H_{23}NO_5$: C, 67.21; H, 6.50; N, 3.93. Found: C, 66.92; H, 6.39; N, 3.85.

A small portion of the 10-alcohol product was recrystallized from benzene to yield a yellow solid whose crystals were suitable for X-ray crystal analysis as well as providing the following additional analytical data. The stereochemistry of the newly installed alcohol is 10-(S), as shown by single crystal X-ray structure determination. This stereochemical outcome is consistent with $H_2O$ attack onto a putative resonance stabilized 10-carbocation from the more sterically accessible face, that which is away from the neighboring amine ring. mp 203–205 ° C (dec.). $^1H$ NMR ($CDCl_3$) δ6.94 (d, 1H, J=9 Hz), 6.82 (d, 1H, J=9 Hz), 5.93–5.79 (m, 1H), 5.30–5.21 (m, 2H), 5.06 (br s, 1H) 4.91 (s, 1H), 4.69 (s, 1H) 3.93 (s, 3H), 3.36 (dd, 1H, J=14, 7 Hz), 3.25 (dd, 1H, J=14, 7 Hz), 3.09–2.97 (m, 2H), 2.62–1.55 (m, 8H). $^{13}C$ NMR ($d_6$-DMSO) δ208.75, 144.21 143.46, 136.32, 129.95, 129.67, 120.87, 117.94, 115.31, 90.39, 70.39, 6 9.47, 62.64, 57.58, 56.74, 51.31, 43.44, 36.54, 32.44, 30.27. UV (MeOH) 283 (1500), 230 (9800) nm. $[\alpha]^{25}_D$ –152° (c 0.220, MeOH). MS (Electrospray) m/z 380 (28%, M+Na$^+$), 358 (base, MH+$^{30}$).

10-(S)-hydroxynaloxone 3-methyl ether (1.1 g, 3.1 mmol) and Dess-Martin periodinane (2.5 g, 5.9 mmol) were stirred in $CHCl_3$ (22 mL) overnight at ambient temperature, then concentrated. The resulting solid was partitioned between EtOAc and 0.5 M NaOH. The organic layer was further extracted with water, half-saturated brine, then dried ($Na_2SO_4$), filtered, and concentrated. The crude product mixture was purified by flash chromatography on silica gel, eluting with a gradient of $CHCl_3$ to 12% EtOAc/$CHCl_3$. The cleanest product fractions were concentrated and dried to provide the ketone (0.70 g, 64%) as a tan crystalline solid, mp 144–152° C. IR υ3384, 1728, 1672 cm$^{-1}$. $^1H$ NMR ($CDCl_3$) indicated 90% ketone purity. Most of this sample was used as is directly in the next step.

A small portion was upgraded to analytical purity by repeating a flash chromatography, this time excluding the few mixed product fractions, concentrating only the purest ones to produce a pale yellow crystalline solid which tenaciously held a trace of $CH_2Cl_2$ used in final sample transfers. mp 150–155° C. $^1H$ NMR ($CDCl_3$) δ7.45 (d, 1H, J=9 Hz), 6.88 (d, 1H, J=9 Hz), 5.88–5.75 (m, 1H), 5.33–5.23 (m, 2H), 4.83 (s, 1H), 4.77 (s, 1H), 4.02 (s, 3H), 3.41–3.34 (m, 1H), 3.18 (s, 1H), 3.11–1.58 (m, 9H). $^{13}C$ NMR ($CDCl_3$) δ206.98, 192.90, 149.95, 144.63, 136.77, 134.02, 123.86, 119.36, 119.31, 115.16, 89.84, 71.14, 71.01, 57.68, 56.92, 52.34, 43.59, 35.91, 31.61, 29.73. UV (MeOH) 323 (6100), 289 (14,000), 243 (14,000), 218 (12,000) nm. $[\alpha]^{25}_D$ –234° (c 0.306, $CH_2Cl_2$). MS (CI, $NH_3$) m/z 356 (base, MH$^+$). HRMS (CI, $NH_3$) m/z (MH$^+$) calcd for $C_{20}H_{22}NO_5$ 356.1498, found 356.1497. Anal. Calcd for $C_{20}H_{21}NO_5$·0.2$H_2O$·0.05 $CH_2Cl_2$: C, 66.30; H, 5.97; N, 3.86; Cl, 0.98. Found: C, 66.35; H, 5.98; N, 3.80; Cl, 1.07.

With the 10-keto group successfully installed, the 3-methyl ether protecting group was cleaved using standard $BBr_3$ conditions. 10-ketonaloxone methyl ether (0.53 g, 1.5 mmol) and 1.0 M BBr₃ in CH₂Cl₂ (1.5 mL) were stirred in chlorobenzene (5 mL) at ambient temperature overnight under N₂. The reaction was quenched with ice cold water (15 mL). The CH₂Cl₂ was distilled out at ambient pressure. The resulting mixture was boiled for 4¾h, then cooled and transferred to a separatory funnel. The organic phase was separated, and the aqueous phase was extracted further with CHCl₃ (2×). The organic layers were discarded. The remaining aqueous phase was adjusted to pH 9.0 by portionwise addition of 1.0 M NaOH, then extracted several times with CHCl₃. The combined organic product solutions were concentrated, then purified by flash chromatography, eluting with a gradient of CHCl₃ to 50% EtOAc/CHCl₃ to 100% EtOAc to 10% MeOH/EtOAc. The major product fractions were combined, concentrated, and dried to yield a pale tan crystalline solid 10-ketonaloxone. As is commonly encountered for deprotection of morphinan alkaloids in this manner, only a 16% yield of the target 10-keto analog was obtained after work-up and flash chromatographic purification. The low isolated product yield was partly due to competitive solubility of zwitterionic phenolic amine in the aqueous phase. (0.14 g, 16%), mp 186–188° C. (dec.). $^1$H NMR (CDCl₃) δ7.41 (d, 1H, J=9 Hz), 6.90 (d, 1H, J=9 Hz), 6.90 (d, 1H, J=9 Hz), 5.88–5.73 (m, 1H), 5.33–5.24 (m, 2H), 4.80 (s, 1H), 3.38 (dd, 1H, J=14, 6 Hz), 3.19 (s, 1H), 3.12–1.59 (m, 9H), O—H signals not seen. $^{13}$C NMR (CDCl₃) δ208.84, 192.63, 146.97, 143.33, 136.76, 133.99, 123.56, 119.90, 119.37, 119.07, 90.05, 71.23, 71.10, 57.70, 52.67, 43.60, 35.96, 31.49, 29.64. IR υ3600–2800, 1732, 1674 cm$^{-1}$. UV(MeOH) 363 (2300), 320 (4800), 291 (8600), 243 (9300) nm. $[\alpha]^{25}_D$-234° (c 0.132, MeOH). MS (Electrospray) m/z 342 (base, MH⁺). HRMS (CI, NH₃) m/z (MH⁺) calcd for $C_{19}H_{20}NO_5$ 342.1341, found 342.1327. Anal. Calcd for $C_{19}H_{19}NO_5 \cdot 0.5H_2O$: C, 65.13; H, 5.75; N, 4.00. Found: C, 65.15; H, 5.56; N. 3.85.

What is claimed is:

1. A method for producing the 10-keto-analog of a compound having a formula selected from formulas I and Ia:

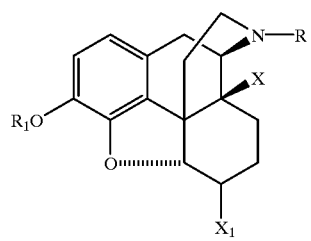

Formula I

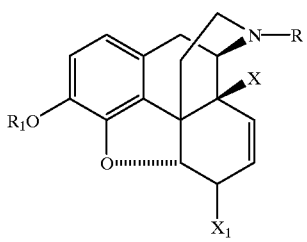

Formula Ia wherein
R is $C_1$–$C_4$ alkyl or alkenyl, $C_3$–$C_4$ cycloalkyl, $C_3$–$C_4$ cycloalkyl alkyl, or $C_3$–$C_4$ cycloalkyl carbonyl
$R_1$ is H or $C_1$–$C_4$ alkyl,
X is H or OH, and
$X_1$ is OH or=O comprising:
mixing said compound with ceric ammonium nitrate in the presence of water, to hydroxylate said compound; and
oxidizing said hydroxylated compound to form the keto-analog of said compound.

2. The method of claim 1 wherein at least one of $R_1$ is H, and $X_1$ is OH, said method further comprising two additional steps, as follows:
prior to the step of mixing, the step of protecting OH groups at the 3- or 6- position to
form a protected compound; and
after the step of oxidizing, the step of restoring said protected OH groups.

3. The method of claim 2 wherein $R_1$ is H, and said step of protecting comprises methylating said OH group.

4. The method of claim 2 wherein $X_1$ is OH, and said step of protecting comprises acetylating said OH group.

5. The method of claim 2 wherein $R_1$ is H and $X_1$ is OH, and said step of protecting comprises methylating the OH group at the 3- position and acetylating said OH group at the 6- position.

6. The method of claim 4 wherein $R_1$ is $CH_3$, and said step of restoring said protected OH group comprises de-acetylating said protected OH group by reaction with a metal hydroxide or carbonate.

7. The method of claim 5 wherein the step of protecting the OH group at the 3- position by converting said OH group to a methoxy group comprises reacting said compound with a methylating agent selected from the group consisting of dimethyl sulfate, methyl iodide, methyl trifluoromethane sulfonate, methyl para-toluene sulfonate, or methyl bromide, in the presence of a base selected from the group consisting of an amine, trialkylamine, sodium hydride, lithium diisopropyl amide, an inorganic base, or an alkalimetal carbonate.

8. The method of claim 7 wherein the step of protecting the OH group at the 6- position by converting said OH group to an acetoxy group comprises reacting said compound with acetic anhydride in the presence of triethylamine and a catalytic amount of 4-dimethyl amino pyridine.

9. The method of claim 5 wherein the step of restoring said protected OH groups by converting said acetoxy and methoxy groups to hydroxy groups consists of reacting said protected compound with a demethylation agent selected from the group consisting of a metal cyanide, a metal halide, a boron trihalide, HF, HCl, HI, HBr, and a mercaptide.

10. The method of claim 1 wherein $R_1$ is H and $X_1$ is =O, said method further comprising additional steps, as follows:
prior to the step of mixing, the step of protecting the OH group at the 3- position by converting said OH group to a methoxy group by reacting said compound with a methylating agent selected from the group consisting of dimethyl sulfate, methyl iodide, methyl trifluoromethane sulfonate, methyl para-toluene sulfonate, or methyl bromide, in the presence of a base selected from the group consisting of an amine, trialkylamine, sodium hydride, lithium diisopropyl amide, an inorganic base, or an alkalimetal carbonate; and
after the step of oxidizing, the step of restoring said protected OH group by converting said methoxy group to a hydroxy group by reacting said protected compound with a demethylation agent selected from the group consisting of a metal cyanide, a metal halide, a boron trihalide, HF, HCl, HI, HBr, and a mercaptide.

11. The method of claim 1 wherein $R_1$ is $CH_3$ and $X_1$ is OH, said method further comprising additional steps, as follows:

prior to the step of mixing:
the step of protecting the OH group at the 6- position by converting said OH group to an acetoxy group to form a protected compound; and
after the step of oxidizing, the step of restoring said protected OH group by converting said acetoxy group to a hydroxy group by reacting said protected compound with a metal hydroxide or metal carbonate.

12. The method of claim 1 wherein said step of oxidizing said hydroxylated compound to form the keto-analog of said compound comprises treating said hydroxylated compound with periodinane.

* * * * *